United States Patent [19]

McCracken et al.

[11] 4,288,594

[45] Sep. 8, 1981

[54] CAUSTIC-FREE PROCESS FOR THE PRODUCTION OF MONOCHLORO-DIAMINO-S-TRIAZINES

[75] Inventors: Philip G. McCracken; Hal Myatt, both of Greensboro; Harris E. Petree, Kernersville, all of N.C.

[73] Assignee: Ciba-Geigy Corporation, Ardsley, N.Y.

[21] Appl. No.: 118,375

[22] Filed: Feb. 4, 1980

Related U.S. Application Data

[63] Continuation of Ser. No. 48,868, Jun. 15, 1979, abandoned, which is a continuation-in-part of Ser. No. 933,375, Aug. 14, 1978, abandoned, which is a continuation of Ser. No. 753,032, Dec. 22, 1976, abandoned.

[51] Int. Cl.³ .......................................... C07D 251/50
[52] U.S. Cl. ..................................................... 544/204
[58] Field of Search ................ 544/194, 197, 204, 211

[56] References Cited

U.S. PATENT DOCUMENTS

| | | | |
|---|---|---|---|
| 3,074,946 | 1/1963 | Rattenbury et al. | 544/201 |
| 3,328,399 | 6/1967 | Prill | 544/204 |
| 3,577,417 | 5/1971 | Cantrall et al. | 544/197 |
| 3,586,679 | 6/1971 | Tandon et al. | 544/194 |

Primary Examiner—John M. Ford
Attorney, Agent, or Firm—Karl F. Jorda

[57] ABSTRACT

A new and improved process is provided for preparing monochloro-diamino-s-triazines which are useful as herbicides.

The process comprises reacting in a first stage cyanuric chloride and a selected monoalkylamine hydrochloride at elevated temperature to give a dichloro-monoalkylamino-s-triazine and reacting in a second stage this dichloro-monoalkylamino-s-triazine with an excess of a different monoalkylamine which may be introduced as a pure liquid, as gas or as a solution in water. The third stage of the process consists of an exchange whereby the monoalkylamine hydrochloride of the first stage and the free monoalkylamine of the second stage are generated. The process gives consistent yields in excess of 97% of monochloro-diamino-s-triazines. Because the process is caustic-free and due to the feasibility of recycling the excess of monoalkylamines employed, no serious effluent problems arise.

12 Claims, No Drawings

CAUSTIC-FREE PROCESS FOR THE PRODUCTION OF MONOCHLORO-DIAMINO-S-TRIAZINES

CROSS-REFERENCE TO RELATED APPLICATIONS

This application is continuation of our application Ser. No. 048,868, filed June 15, 1979, now abandoned, which is a continuation-in-part of our application Ser. No. 933,375, filed Aug. 4, 1978, now abandoned, which is a continuation of our application Ser. No. 753,032, filed Dec. 22, 1976, now abandoned.

BACKGROUND OF THE INVENTION

1. Field of the Invention

The present invention relates to a new and improved procedure for the preparation of monochloro-diamino-s-triazines of known herbicidal activity. The monochloro-diamino-s-triazines are obtained by the present procedure not only in high yield and excellent product quality, but also without giving rise to problems in effluent treatment and disposal.

2. Description of the Prior Art

The herbicidal activity of various monochloro-diamino-s-triazines has been described, for example, in Gysin et al. U.S. Pat. No. 2,891,855. One such monochloro-diamino-s-triazine, which is commercially useful as a herbicide, is 2-chloro-4-ethylamino-6-isopropylamino-s-triazine. This compound is commercially available as an atrazine herbicide. The aforesaid 2-chloro-4-ethylamino-6-isopropylamino-s-triazine can, as described in the Gysin et al. patent referred to above, be prepared from cyanuric chloride and the corresponding organic amines.

The synthesis ordinarily proceeds via the formation of the 2,4-dichloro-6-isopropylamino-s-triazine intermediate compound in accordance with the following reaction:

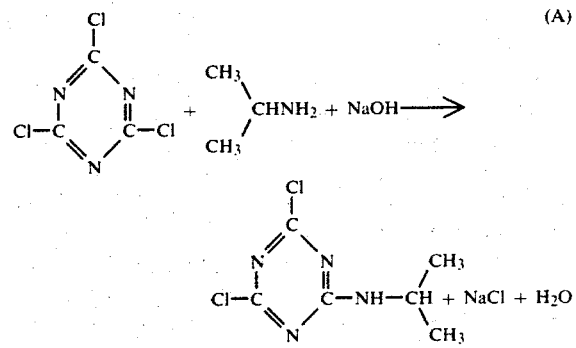

(A)

The 2,4-dichloro-6-isopropylamino-s-triazine compound is thereafter converted to the active compound, i.e., 2-chloro-4-ethylamino-6-isopropylamino-s-triazine, referred to as atrazine, by reaction with monoethylamine, as follows:

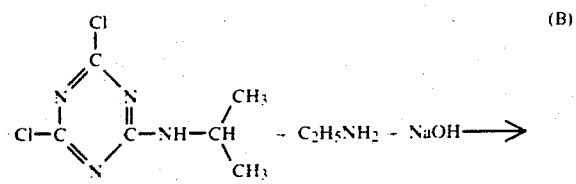

(B)

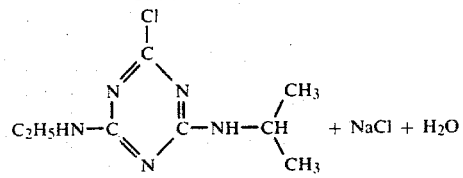

The first step (equation A above) is accompanied by a number of undesirable side reactions, which may for example involve the hydrolysis of some of the chloroamino-s-triazines or the formation of various by-products, such as, 2-chloro-4,6-bis-isopropylamino-s-triazine. The undesired formation of the last mentioned material, where the preparation of the atrazine product is concerned, may proceed in accordance with the following reaction scheme:

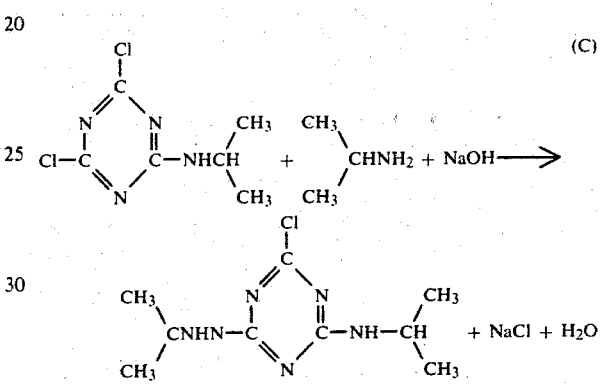

(C)

In the preparation of 2-chloro-4,6-diamino-s-triazines and, by way of illustration, of the atrazine herbicide, i.e., 2-chloro-4-ethylamino-6-isopropylamino-s-triazine, it will be appreciated that it is desirable to minimize the co-production of the by-product illustrated in equation (C) and of other by-products, thereby avoiding difficulties in isolating the desired atrazine product when said product is produced on a large scale. It is also highly desirable to produce the 2-chloro-4,6-diamino-s-triazines in high yield and purity without creating problems in effluent treatment and disposal because of the aqueous NaCl and triazine by-products contained in the aqueous effluent of the above described process of manufacture.

U.S. Pat. No. 3,328,399 discloses a process for preparing amino-s-triazines without neutralizing the HCl formed in the reaction. However, this patent discloses only a method involving reacting cyanuric chloride with secondary amines in an anhydrous system and the HCl formed is distilled off from the reaction mixture.

This method of amino-s-triazine preparation cannot be extended to monoalkylamines. Unhindered monoalkylamine hydrochlorides can react under the conditions described to form bistriazines, a reaction not possible with secondary amines;

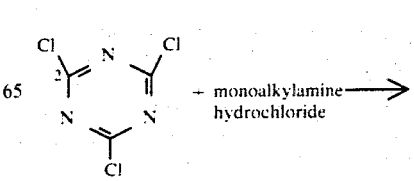

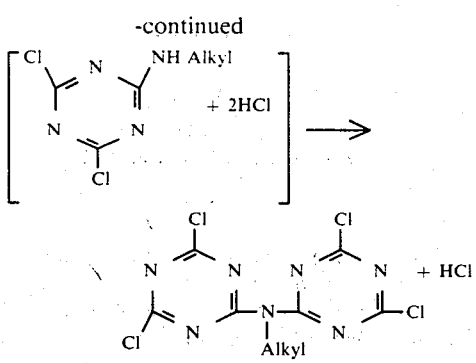

In addition, as the reactivities of the second and third chlorine on the cyanuric chloride molecule are not substantially different, monoalkylamines do not exhibit sufficient selectivity to stop after substitution of two chlorines; rather a mixture of mono-, di-, and tri-substituted triazines is formed in contrast to the selectivity of the less reactive secondary amines:

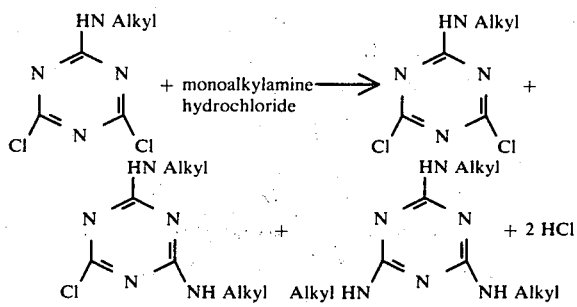

Unhindered monoalkylamines may form bis-triazines in the second stage also as shown:

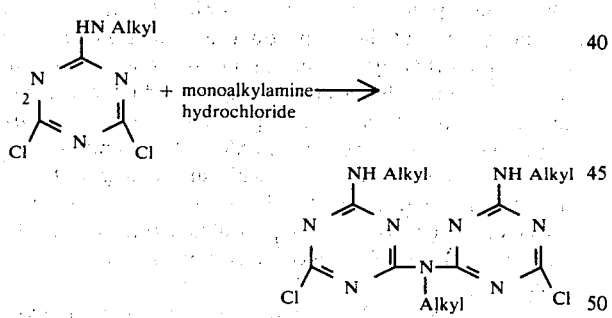

The lack of selectivity of monoalkylamines in the second step of the reaction and the tendency to form bis-triazines in both stages precludes atrazine-type herbicides by the conditions of U.S. Pat. No. 3,328,399.

And U.S. Pat. No. 3,586,679 discloses a process for the production of only dichloro-monoamino-s-triazines in an anhydrous medium with no provision for conversion to monochloro-diamino-s-triazines in a caustic-free manner.

DETAILED DISCLOSURE

In the present invention, monochloro-diamino-s-triazines are produced in high yield and purity, with a reduced consumption of energy and reactants and no consumption of acid acceptor, by a process which comprises initially reacting in a batch or continuous manner, at elevated temperature, cyanuric chloride with a corresponding monoalkylamine hydrochloride according to the following reaction scheme:

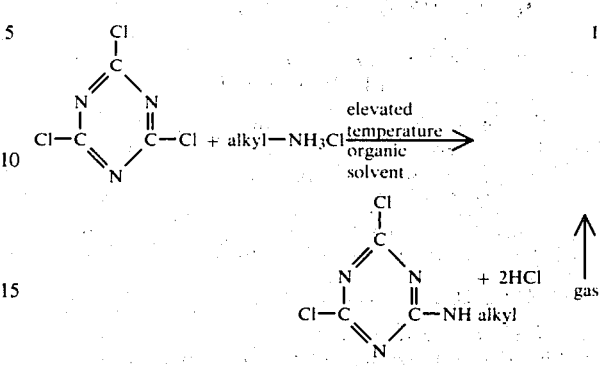

and with concomitant evolution of two moles of hydrogen chloride gas.

Examples of preferred monoalkylamine hydrochlorides are the hydrochlorides of: n-propylamine, isopropylamine, 1,2-dimethyl-n-propylamine, 1-methyl-2-methoxy-ethylamine, sec-butylamine, tert-butylamine. The process step I is performed at a reaction temperature between about 90° and 200° C., preferably between 120° and 150° C., at normal or elevated pressure, e.g., 1 to 10 atmosphere, and preferably in an inert solvent or diluent. Suitable solvents or diluents for this process step are aromatic hydrocarbons, for example, toluene, o-xylene, m-xylene, p-xylene or mixtures thereof, or chlorinated aliphatic or aromatic hydrocarbons, such as tetrachloroethylene or monochlorobenzene, or aliphatic hydrocarbon solvents of suitable boiling range.

The second step substitution of the dichloro-alkylamino-s-triazine intermediate is carried out at a reduced temperature between about 40° and 100° C., preferably between 50° and 80° C., and at normal pressure in a batch or continuous manner. In this step, the further alkylamine substitution is carried out by adding an excess of monoalkylamine (preferably 1 equivalent) in anhydrous gaseous or liquid form or as aqueous solution, e.g., as an approximately 70% solution in water. One equivalent of monoalkylamine acts thereby as an acid acceptor, forming one equivalent each of the active monochloro-diamino-s-triazine (e.g. 2-chloro-4-ethylamino-6-isopropylamino-s-triazine→atrazine) and monoalkylamine hydrochloride, which is dissolved in the lower aqueous layer and removed by drawing off this layer. This reaction step can be depicted as follows:

-continued

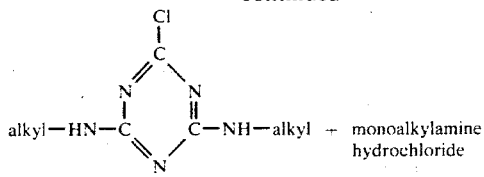 → monoalkylamine hydrochloride

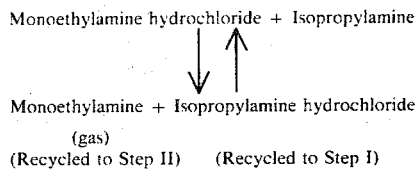

(gas)
(Recycled to Step II)    (Recycled to Step I)

The monoalkylamine hydrochloride formed, if anhydrous instead of aqueous monoalkylamine is used, may also be removed as a melt at a temperature sufficiently high so that the monoalkylamine hydrochloride is at or above its melting point, (e.g., at about 110° C. or greater in the case of monoethylamine hydrochloride), but provision must be made to minimize formation of tris-(alkylamino)-s-triazine compounds, e.g., by rapid heating with the use of, e.g., a coalescer or decanter, to separate the monoalkylamine hydrochloride, followed by rapid cooling. The by-product monoalkylamine hydrochloride may further be removed as a soluble extract in polyhydroxy or polyether solvents selected from, e.g., ethylene glycol, glycerine, diethylene glycol or polyethylene glycol.

While the above reaction can be carried out using 2 moles of anhydrous monoalkylamine, which is different from the monoalkylamine used for step I, an undesirable side-reaction occurs at a significant rate between the active monochloro-diamino-s-triazine and anhydrous monoalkylamine or monoalkylamine hydrochloride, resulting in the formation of tris-(alkylamino)-s-triazine compounds, which are yield-losing and undesirable products in the effluent.

Therefore, it is preferable that water be added to have a partially aqueous monoalkylamine solution so that the formation of tris-(alkylamio)-s-triazine compounds in the side-reaction is much lower and results in only approximately 0.2 to 0.8% or less of these by-products.

It is also of great significance that the small amount of tris-(alkylamino)-s-triazines as impurity is found mostly in the monoalkylamine hydrochloride/water layers and in successive aqueous extractions.

The organic solvent layer containing up to 25% of monochloro-diamino-s-triazine (active product) may be freed of solvent by steam stripping to leave a water/monochloro-diamino-s-triazine slurry from which the monochloro-diamino-s-triazine product is isolated by filtration (for subsequent grinding and formulation). Alternatively, the bulk of the monochloro-diamino-s-triazine may be removed from the organic solvent layer by cooling to crystallize the active product, which is filtered off to leave a more dilute organic solution. This latter may be further treated to recover additional monochloro-diamino-s-triazine or it may eventually by recycled to the first or second stage of the reactor system.

The third step of the process is to regenerate the amine hydrochloride of step I and the free amine of step II without consuming an acid acceptor. As in the case of 2-chloro-4-ethylamino-6-isopropylamino-s-triazine (atrazine) the monoethylamine hydrochloride obtained as a solution or melt from step II is mixed with an excess of isopropylamine and free monoethylamine (bp 16.6° C.) is removed from the mixture by an efficient fractionation column to give a pot mixture of excess isopropylamine (bp 33° C.) and isopropylamine hydrochloride with free monoethylamine as the overhead product.

An alternative to distillative exchange of amine may be exchange via a suitable ion-exchange medium.

The exchange may be accomplished either with the aqueous monoethylamine hydrochloride extract or with monoethylamine hydrochloride which remains after azeotropic drying with the organic solvent layer. Thereby, the isopropylamine hydrochloride (after fractionation) in the water layer may be treated to remove its tris-(alkylamino)-s-triazine impurities. An alternative is to remove the tris-(alkylamino)-s-triazine impurities prior to amine exchange. The separation of tris-(alkylamino)-s-triazine impurities from ethylamine hydrochloride/water solution and from successive aqueous extracts may be achieved by several methods known in the art, such as, extraction with a solvent ($CH_2Cl_2$, $CHCl_3$, $CCl_4$, toluene or xylene, etc.), or by filtration after an interval of time to allow the tris-(alkylamino)-s-triazines to precipitate, or by absorption on activated material (e.g., carbon) or by ion-exchange techniques. The final, purified isopropylamine hydrochloride/water layer is then dried by removing the water as an azeotrope in an organic solvent to leave a slurry of isopropylamine hydrochloride in the organic solvent which is recycled to the feed of the first step (I) reactor. The fractionated purified monoethylamine may be compressed and stored and then absorbed in water to form the desired concentration of monoethylamine/water for feeding to the second stage (II) reaction above. Direct absorption of the anhydrous monoethylamine in water is another possible means of recycling the monoethylamine.

It is to be noted that the total summation of reactions, I, II and III above is one in which no caustic or other acid acceptor is consumed: cyanuric chloride+isopropylamine+monoethylamine→2-chloro-4-ethylamino-6-isopropylamino-s-triazine+2 HCl (gas).

Thus, this invention provides a non-caustic-consuming process for manufacturing monochloro-dialkylamino-s-triazine herbicides, such as atrazine, which has, as by-product, anhydrous hydrogen chloride gas. The gaseous hydrogen chloride has economic value as a chemical intermediate per se, or it may be used in a number of processes for the economic production of chlorine gas. In addition, the process of this invention makes it possible to manufacture for example 2-chloro-4-ethylamino-6-isopropylamino-s-triazine, with a very large reduction in the amount of total effluent normally consisting of very large volumes of aqueous salt solution from the neutralization of HCl with caustic and which also contains small amounts of triazine impurities. These impurities, consisting of such by-products as hydroxy-triazines and tris-(alkylamino)-s-triazine, would be very expensive to remove completely from a large volume of aqueous saline effluent. A lower total energy consumption might be expected on account of the reduction in the present high consumption of electricity for the intense cooling needed to lower reactor temperatures as in the cyanuric chloride/toluene: caustic/water reaction system. The totaly yields of monochloro-dialkylamino-s-triazine range from 97.5 to 99.5% (based on cyanuric chloride) of product containing, e.g., 97 to 99% of 2-chloro-4-ethylamino-6-isopropylamino-s-triazine, as well as the low "active" by-product formation of 0.5 to 1% of 2-chloro-4,6-bis(isopropylamino)-s-triazine and 0.5 to 1.5% of 2-chloro-4,6-bis(ethylamino)-s-triazine; and the formation of inactive by-products (or effluent impurities) is from 0 to 0.1% of hydroxy-triazines and 0.2 to 0.8% of tris-(alkylamino)-s-triazines (much of this undesirable by-product can be recovered for disposal by additional aqueous extractions after removal of the monoethylamine hydrochloride layer).

It can thus, on balance, be demonstrated that the very high conversion of cyanuric chloride to a marketable product makes the caustic-free process for the manufacture of amino-s-triazines economically very advantageous. In addition, effluent treatment costs are very substantially lower compared with those for an aqueous caustic/toluene reaction system due to very greatly reduced volumes of aqueous effluent. Also the elimination of caustic or other acid acceptor results in substantial raw material savings.

The following non-limitative examples will serve to illustrate the process of the invention.

EXAMPLE 1

(a) A 2-liter, 3-neck bottom outlet reactor was equipped with thermometer, mechanical stirrer and Dean-Stark trap, with a $N_2$ sweep over the condenser. Into the flask was charged isopropylamine hydrochloride (63.11 g; 0.65 mole) and 1000 ml of xylene. The mixture was then refluxed for 30 minutes to ensure dryness. The mixture was cooled to approximately 65° to 70° C., then cyanuric chloride (119.86 g; 0.65 mole) was added, and an additional 225 ml of xylene. The Dean-Stark trap was replaced with a reflux condenser with a nitrogen sweep vented to a hood or NaOH trap. The reaction mixture was then heated to reflux, and it was observed that HCl began to evolve at approximately 105° C., with the major portion of this evolution of HCl occurring at 130° to 140° C. The mixture was kept at reflux until HCl evolution had ceased and the mixture was clear (about 2 to 2.5 hours). Care was taken to react the hydrochloride completely from the reactor walls and stirrer shaft.

(b) The reaction mixture was then cooled to 65° C. and monoethylamine (83.57 g of 70% aqueous solution; 1.30 mole) was added dropwise in the course of 30 minutes at 65° to 70° C. The reaction mixture was then stirred for 30 minutes, then heated to form a two-phase solution. The lower aqueous phase was drawn off, then the xylene was removed by steam stripping. The solid product was collected by filtration and dried under vacuum for 12 hours at 60° C. Yield: 138.37 g of product containing 97.6% of 2-chloro-4-ethylamino-6-isopropylamino-s-triazine, 0.90% of 2-chloro-4,6-bis(isopropylamino)-s-triazine (propazine), 0.95% of 2-chloro-4,6-bis(ethylamino)-s-triazine (simazine) and 0.79% of 2,4-dichloro-6-isopropylamino-s-triazine. Trialkylamino- and hydroxy-triazines were present in an amount of less than 0.05% each. The isolated yield of herbicides was 98.15%.

(c) The aqueous monoethylamine hydrochloride extract was extracted once with chloroform, then dried by azeotropic distillation with toluene. The salt was then cooled, filtered and dried to yield 51.50 g of monoethylamine hydrochloride with a melting point of 108° to 110° C. Yield = 97.3%.

(d) To a 250 ml round bottom flask equipped with stirrer, thermometer, and condenser topped with Dean Stark trap was charged 16.05 g monoethylamine hydrochloride, 11.6 g isopropylamine and 125 ml xylene. The mixture was heated while 11.6 g addition isopropylamine was added dropwise to the flask. Free amines were collected in the Dean-Stark trap. When the pot temperature reached 125° C. the slurry was cooled and filtered. The dried product isopropylamine hydrochloride melted at 153°–154° C. (Lit 153°–155° C.) and was suitable for recycle to step I. Monoethylamine was not detected by gas chromotography. Yield = 96.7%. The overhead contained a mixture of monoethylamine and isopropylamine, easily separated by fractional distillation.

EXAMPLE 2

(Illustration of the Removal of MEA.HCl as a Melt only)

A 2-liter, 3-neck bottom outlet reactor equipped with mechanical stirrer, reflux condenser and thermometer was charged with cyanuric chloride (184.4 grams, 1.0 mole) and one liter of xylene. The mixture was cooled to 0° C. and isopropylamine (59.1 grams, 1.0 mole) was added dropwise maintaining a temperature below 0° C. When the addition was complete, the mixture was refluxed for 2 hours with evolution of HCl.

The resultant solution was cooled to 55° and anhydrous monoethylamine (90.0 grams, 2.0 moles) was added dropwise between 55°–70° C. When the addition was complete, the mixture was heated to 120° C., and the lower layer of molten monoethylamine hydrochloride drawn off. The xylene was then removed by steam stripping, and the product collected by filtration and dried. The yield was 209.93 grams of a product containing 96.4% atrazine, 1.59% propazine, and 1.17% simazine. The isolated yield of herbicide was 96.4% on cyanuric chloride.

79.84 grams of monoethylamine hydrochloride was recovered for a yield of 98.9%.

EXAMPLE 3

A 2-liter 3-neck bottom outlet reactor was equipped with thermometer, mechanical stirrer and Dean-Stark trap, with a $N_2$ sweep over the condenser. Into the flask was charged ispropylamine hydrochloride (63.11 grams, 0.65 m) and 1000 ml of xylene. The mixture was refluxed for 30 minutes with azeotropic removal of water to insure dryness. The mixture was cooled to approximately 65°–70° C., then cyanuric chloride (119.86 gr., 0.65 m) was charged, with an additional 225 ml of xylene. The Dean-Stark trap was replaced with a reflux condenser with a nitrogen sweep vented to a hood. The reaction mixture was then heated to reflux and maintained at reflux until HCl evolution ceased and mixture was clear, about 2 to 2.5 hours.

The reaction mixture was then cooled to 70° C. and anhydrous monoethylamine (58.5 grams, 1.30 mole) was added dropwise between 60° and 70° C. When the addition was complete, 95 grams of glycerine was added. The mixture was then heated to 95° C., and the lower glycerine layer drawn off. The xylene was then steam-distilled, and the product collected by filtration and dried. The yield was 138.0 grams of a solid containing 96.6% atrazine, 1.67% propazine, 0% simazine. The isolated yield of herbicide was 96.8%. 146.32 grams of glycerinemonoethylamine hydrochloride solution was obtained, corresponding to a yield of 97% of monoethylamine hydrochloride.

EXAMPLE 4

To a continuous reactor train consisting of two one-liter bottom outlet reactors, transfer and addition pumps, and condensers, was charged a slurry of isopropylamine hydrochloride in xylene at the rate of ¼ mole/hour. Simultaneously was added a solution of cyanuric chloride in xylene, also at the rate of ¼ mole/hour. A total residence time of 1.5 hours was maintained, the temperature was held at about 140° C. A total of one mole of each reactor was charged continuously over a 4 hour period. The resultant dichloro-isopropylamino-s-triazine solution was then converted to atrazine by addition of two equivalents of monoethylamine. Products were isolated as described in Example 1 above. The isolated yield of herbicide was 96.4% on cyanuric chloride, consisting of 93.2% atrazine, 1.22% propazine, and 3.96% simazine.

The invention has been illustrated by way of a few preferred embodiments. It is to be understood, however, that such modifications and variations as would be obvious to persons skilled in the art are within the scope of the appended claims.

What we claim is:

1. A three-stage process for the preparation of a monochloro-diamino-s-triazine which comprises:
   (a) reacting at elevated temperature and normal or elevated pressure, and in an organic solvent, cyanuric chloride and a monoalkylamine hydrochloride in substantially stoichiometric amounts to form 2,4-dichloro-6-alkylamino-s-triazine and two moles of HCl gas,
   (b) reacting the solution of step a) at a less elevated temperature and normal pressure with 100% or greater excess of a different monoalkylamine to form a monochloro-diamino-s-triazine and monoalkylamine hydrochloride, and
   (c) distillatively exchanging the monoalkylamine hydrochloride obtained in step b) with the monoalkylamine in step (a) to generate the monoalkylamine hydrochloride needed in step (a) and the free monoalkylamine needed in step (b).

2. A process according to claim 1, wherein the reaction of step (a) is performed at a temperature between 90° and 200° C., in an aromatic hydrocarbon or aliphatic hydrocarbon or chlorinated aliphatic hydrocarbon or chlorinated aromatic hydrocarbon solvent and at normal pressure or at a pressure of 1 to 10 atmospheres, and the reaction of step (b) is performed at a temperature between 40° and 100° C.

3. A process according to claim 2, wherein the reaction of step (a) is performed at a temperature between 120° and 150° C., in a solvent selected from toluene, o-xylene, m-xylene, p-xylene, or a mixture thereof, or monochlorobenzene or tetrachloroethylene and the reaction of step (b) is performed at a temperature of 50° to 80° C.

4. A process according to claim 1, wherein the 100% or greater excess of monoalkylamine in step (b) is in aqueous solution.

5. The process according to claim 4, wherein the monoalkylamine hydrochloride by-product is removed by drawing off the aqueous layer wherein it is dissolved.

6. A process according to claim 1, wherein the 100% or greater excess of monoalkylamine in step (b) is charged in anhydrous gaseous or liquid form.

7. A process according to claim 6, wherein the monoalkylamine hydrochloride by-product is removed as a molten liquid at a temperature at least as high as its melting point, with rapid heating to melt temperature and rapid cooling after drawing off the melt.

8. A process according to claim 6 wherein the monoalkylamine hydrochloride by-product is removed as a soluble extract in polyhydroxy or polyether solvents selected from ethylene glycol, glycerine, diethylene glycol or polyethylene glycol.

9. A process according to claim 1, wherein the monoalkylamine hydrochlorides of step (a) are selected from the hydrochlorides of n-propylamine, isopropylamine, 1,2-dimethyl-n-propylamine, 1-methyl-2-methoxyethylamine, sec-butylamine, tert. butylamine.

10. A process according to claim 1, wherein the monoalkylamines of step (b) are selected from methylamine, ethylamine, n-propylamine, isopropylamine, 1,2-dimethyl-n-propylamine, 1-methyl-2-methoxyethylamine, sec-butylamine, tert-butylamine.

11. A process according to claim 1, wherein the monoalkylamine hydrochloride of step (a) is isopropylamine hydrochloride and the monoalkylamine of step (b) is ethylamine.

12. A process according to claim 1, wherein 2-chloro-4-ethylamino-6-isopropylamino-s-triazine is prepared.

* * * * *